US00PP32105P2

(12) United States Plant Patent
Hansen

(10) Patent No.: US PP32,105 P2
(45) Date of Patent: Aug. 18, 2020

(54) *ECHINACEA* PLANT NAMED 'ORANGE YOU AWESOME'

(50) Latin Name: ***Echinacea* hybrid**
Varietal Denomination: Orange You Awesome

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/602,726

(22) Filed: Nov. 26, 2019

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428
CPC ..... A01H 5/02; A01H 6/14
See application file for complete search history.

*Primary Examiner* — Annette H Para

(57) ABSTRACT

The new and distinct cultivar of *Echinacea* plant named 'Orange You Awesome', with fragrant inflorescences on strong branched stems producing single whorls of bright orange ray florets that maintain their coloration through maturity. The large inflorescence cones have pronounced chaff with effective colors ranging from greyed-purple to reddish orange. The new plant flowers from mid-summer to late summer, and is suitable as a potted plant, for the landscape, and for cut flower arrangements.

1 Drawing Sheet

Botanical denomination: *Echinacea* hybrid.
Cultivar designation: 'Orange You Awesome'.

STATEMENT REGARDING PRIOR DISCLOSURES UNDER 37 CFR 1.77(B)(6)

The first public disclosure of the claimed plant, in the form of a photograph and brief description on a website operated by Walters Gardens, Inc. on Dec. 1, 2018. *Echinacea* 'Orange You Awesome' was listed with a photograph and brief description in the "Walters Gardens 19-20 Catalog" distributed first on May 29, 2019. The claimed plant was first sold on Jul. 8, 2019 by Walters Gardens, Inc., who obtained the plant and all information relating thereto, from the inventor. No plants of *Echinacea* 'Orange You Awesome' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of Coneflower from the genus *Echinacea* and given the cultivar name 'Orange You Awesome'. The new plant was the result of a self-pollination by the inventor of an unnamed proprietary hybrid known as 14-6-88 (not patented) on Jul. 15, 2015 at a wholesale perennial nursery in Zeeland, Mich. This seedling was evaluated first in trials in the summer of 2016 at the same nursery and assigned the breeder code of 15-7-2. *Echinacea* 'Orange You Awesome' has been asexually propagated at the same nursery by crown division since 2017 and also using careful shoot tip tissue culture procedures and found to reproduce plants that exhibit all the characteristics identical to the original plant.

*Echinacea* 'Orange You Awesome' is distinct from all other Coneflowers known to the inventor. The nearest comparison cultivars are 'Atomic Orange' U.S. Provisional Patent No. 62/918,484, 'Balsomador' U.S. Plant Pat. No. 26,639, 'Julia' U.S. Plant Pat. No. 24,629, 'Flame Thrower' U.S. Plant Pat. No. 21,932, 'Tiki Torch' U.S. Plant Pat. No. 18,839, 'TNECHKIO' U.S. Plant Pat. No. 28,769.

The parent plant, 14-6-88, was not maintained as either plants or in photography, so no comparison is possible. 'Atomic Orange' is slightly shorter in habit and the ray florets are more reddish-orange. 'Balsomador' is slightly smaller in habit and ray florets have a more reddish-orange overlay. 'Julia' has narrower ray florets that are less overlapping and more greyed-orange to reddish-orange watermelon pink on taller plants. 'Flame Thrower' produces much taller and broader plants with ray petals that cup down producing duller ray florets with more greyed orange to orangish-yellow. 'Tiki Torch' is much taller in habit, the inflorescences are smaller and the ray florets are orangish-pink. 'TNECHKIO' has much shorter habit, smaller inflorescences and the ray petals are more reddish-orange.

SUMMARY OF THE INVENTION

*Echinacea* 'Orange You Awesome' has not been evaluated under all possible environmental conditions. The phenotype may vary with variations in environment including: growing temperature, available sunlight, nutrients, water, etc. without a change in the genotype of the plant. The new plant is distinct from its parents and all other *Echinacea* known to the applicant in the following combined traits:

1. Fragrant inflorescences on strong branched stems;
2. Large, broad inflorescences with single whorl of ray florets that tend to stay horizontal once open;
3. Ray petals of bright orange with dark cones;
4. Vigorous growth and excellent habit;
5. Greyish, olive-green ovate foliage.

BRIEF DESCRIPTION OF THE DRAWINGS

The photographs of the new invention demonstrate the overall appearance of the plant including the unique traits.

The drawings of the new plant are of a two-year-old plant grown in full-sun trial garden in Zeeland, Mich. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
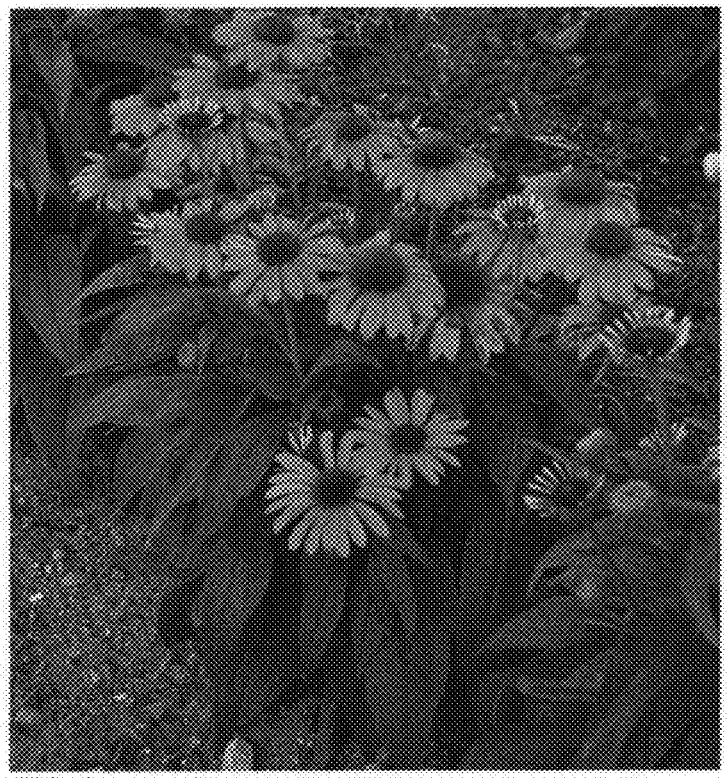
FIG. 1 shows the habit of the new plant in flower.
Figure 2:
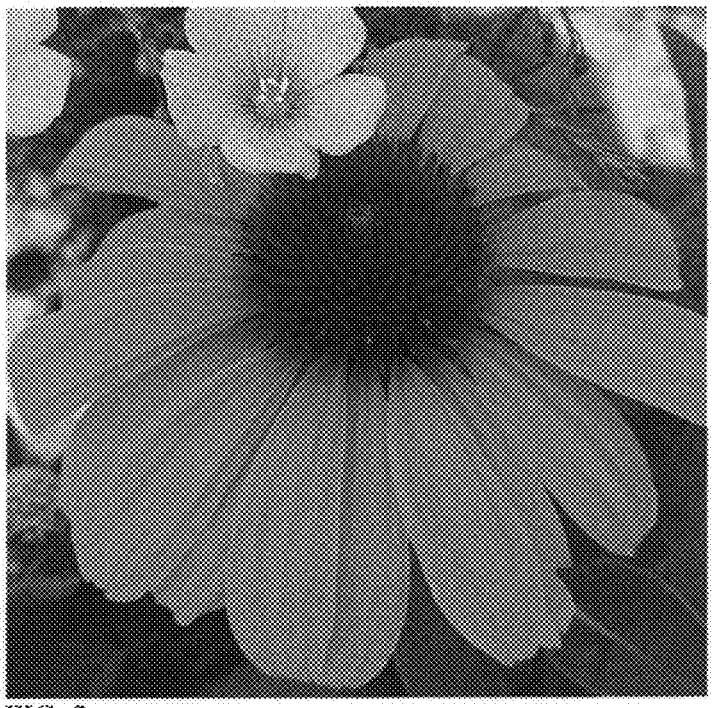
FIG. 2 shows a close up of some inflorescences of the new plant.

The following description of *Echinacea* 'Orange You Awesome' is based on observations of two-year-old specimens grown in a full-sun trial garden with supplemental water and fertilizer in Zeeland, Mich. The new plant has not been tested in all environments and some phenotypic differences may occur with different environments without, however, any change in genotype. The color descriptions are based on the 2015 edition of The Royal Horticultural Society Colour Chart except where common dictionary descriptions are used.

Parentage: Female and male parent is the proprietary unreleased hybrid 14-6-88;

Plant habit: Multi-stemmed, freely-branched, hardy herbaceous perennial, flowering to about 51 cm tall and foliage to 34 cm tall and 56 cm wide;

Growth rate: Vigorous, finishing in 4 liter containers in about 2 months during the summer;

Roots: Cream-colored, finely branched;

Foliage: Alternate; ovate; acute apex; attenuate base; margin dentate, micro-ciliolate; hirsutulous abaxial and adaxial; to about 20.0 cm long and 10.8 cm wide decreasing distally, average about 15.5 cm long and 8.8 cm wide;

Leaf color: Young leaves adaxial nearest RHS 146B, abaxial nearest RHS 146D; mature leaves adaxial nearest NN137A, abaxial nearest RHS 147B;

Foliage fragrance: Lightly herbal;

Venation: Pinnate; with two major arcuate veins on both sides of the midrib; abaxial midrib and veins costate; glabrate to glabrous adaxial, sparsely hirsutulous abaxial;

Vein color: Adaxial primary veins between RHS 138B and RHS 138C, secondary nearest RHS NN137A; abaxial primary veins between RHS 146D and RHS 145A, secondary nearest RHS 137A;

Petiole: Concavo-convex, strigillose adaxial and sparsely puberulent to strigillose abaxial; about 11.5 cm long and 3.0 mm wide on lowest leaves and decreasing to sessile distally; color nearest RHS 146D adaxial and abaxial nearest RHS 145A;

Peduncle: Strigillose; cylindrical; strong stiff; average 20.0 cm long and 10.0 mm diameter; quantity per plant about seven; flowering in upper 36 cm;

Peduncle color: Nearest RHS 146C;

Branches: Cylindrical, strigillose; tightly angled to main stem to about 60° above horizontal: to about 30 cm long and 4.5 mm diameter; color between RHS 145A and RHS 146D;

Inflorescence: Bracteate head, aggregate of achene; with single whorl of distinct ligulate ray florets and disk florets in a pappus; flowering mid-summer to late summer; initial flowers largest, to about 12.5 cm wide, average about 11.0 cm diameter with cones 4.0 cm across and 4.5 cm tall; approximately 7 inflorescences per peduncle;

Inflorescence fragrance: Lightly sweet;

Flower persistence: Remaining affective in color for 10 to 14 days depending on temperatures, cone drying on plant and effective into winter;

Involucre: With numerous bracts, about 68 per inflorescence in 4 whorls; arcuate downward toward peduncle;

Involucre bracts: Lanceolate to linear; narrowly acute apex; truncate base; micro-ciliolate margin; adaxial glabrous; abaxial strigillose; average about 13.0 mm long and 3.0 mm across; color nearest RHS 138A adaxial center, abaxial center nearest RHS 137A, adaxial and abaxial margins nearest RHS 146D;

Inflorescence buds with ray florets vertical and still enrolled: About 35.0 mm across and 25.0 mm tall; ray floret color between RHS 181C and RHS 182B with spines nearest RHS 183C;

Ray florets: Zygomorphic; arrangement in single whorl, frequently imbricate; lanceolate, apex emarginated with two or more notches to 1.0 mm deep; base attenuate; margin entire; adaxial lustrous; abaxial matte; 16 to 24 per inflorescence; opening to horizontal, drooping up to only 15 degrees below horizontal with maturity; astemonous; ligule to 52.0 mm long and 14.0 mm wide, average size 46.0 mm long, 12.5 mm wide at center tapering to 2 mm wide at base; thickened veins raised;

Ray ligule color: Consistent through maturity; adaxial basal 6.0 mm nearest RHS 60C, distal one-half nearest RHS N25B with region between nearest RHS N163A; abaxial base lighter than RHS 146D, outside margin nearest RHS 71A and center nearest a blend of RHS 61B, RHS 29D and RHS 25D, apex nearest RHS 145B;

Disc florets: About 275 to 450 per head; actinomorphic; perfect; synandrous; produced in raised dome, about 4.5 cm across and 4.0 cm tall;

Corolla: Fused forming tube; outer florets about 8.0 mm long and 2.0 mm wide, central florets about 9.0 mm long and 2.0 mm wide, fused in basal 7.0 to 8.0 mm, free in distal 1.0 mm; individual tepals about 0.5 mm wide at fusion; acute apex; entire margin; surfaces slightly lustrous;

Corolla tube color: Adaxial and abaxial nearest RHS 146C except nearest RHS 185A in distal 1.0 mm;

Disk floret androecium: Five; synandrous;

Staminal column: About 0.7 mm wide and protrudes from corolla tube about 2 mm; five fused stamens;

Anthers: Fused, about 4.0 mm long and 0.7 mm diameter; color between RHS N187A and RHS 202A;

Filaments: Five; attached to column; thin, less than 0.2 mm diameter and 0.5 mm long; color nearest RHS 158D;

Pollen: Globose, less 0.1 mm in diameter, RHS 17B;

Gynoecium: Single; to 9.0 mm long;

Style: About 7.5 mm long and 0.3 mm diameter; color nearest RHS 145C distally and RHS 145D proximally;

Stigma: Bifid; about 1.5 mm long and 0.3 mm diameter; color nearest RHS N186C;

Fruit: Achene; pyramidal; about 4 mm long and 3 mm wide; acute base and fringed flattened apex; color variable nearest RHS 199D and between RHS 202A and RHS 202B;

Receptacle pines: With disk florets; acicular; to 16 mm long and 2.0 mm across;

Spine color: Upon opening apices nearest RHS 187C with bases nearest RHS 144A; mature flower apices nearest RHS 187A, next distal 2.0 mm between RHS 178B and RHS 172B, midsection nearest RHS 137B and base nearest RHS 145D; after ray ligules fall apices nearest RHS 183A, midsection nearest RHS 146D with base nearest RHS 145D; after dried base nearest RHS N200A and distal 5.0 mm nearest RHS 202A;

Disease resistance: Resistance beyond that of other hardy Coneflower cultivars has not been observed. The plant grows best with plenty of moisture and adequate drainage, but is able to tolerate some drought when mature. Hardiness at least from USDA zone 4 through 8.

I claim:

1. A new and distinct cultivar of *Echinacea* plant named 'Orange You Awesome' as herein described and illustrated.

* * * * *